United States Patent
Johnson et al.

(10) Patent No.: US 7,220,872 B2
(45) Date of Patent: May 22, 2007

(54) CONVERSION OF TAXANE MOLECULES

(75) Inventors: James H. Johnson, Merrimac, MA (US); Rex T. Gallagher, Beverly, MA (US); Roland R. Franke, Gloucester, MA (US)

(73) Assignee: Natural Pharmaceuticals, Inc., Beverly, MA (US)

( * ) Notice: Subject to any disclaimer, the term of this patent is extended or adjusted under 35 U.S.C. 154(b) by 0 days.

(21) Appl. No.: 10/510,120

(22) PCT Filed: Apr. 5, 2003

(86) PCT No.: PCT/US03/10557

§ 371 (c)(1),
(2), (4) Date: Oct. 4, 2004

(87) PCT Pub. No.: WO03/087079

PCT Pub. Date: Oct. 23, 2003

(65) Prior Publication Data

US 2005/0234249 A1    Oct. 20, 2005

Related U.S. Application Data

(60) Provisional application No. 60/370,583, filed on Apr. 5, 2002.

(51) Int. Cl.
*C07D 305/00* (2006.01)
*C07D 407/00* (2006.01)
*C07D 493/00* (2006.01)

(52) U.S. Cl. .................................. 549/511; 549/510
(58) Field of Classification Search .............. 549/510, 549/511
See application file for complete search history.

(56) References Cited

U.S. PATENT DOCUMENTS

| 5,319,112 | A | * | 6/1994 | Kingston et al. | 549/510 |
| 5,679,807 | A | * | 10/1997 | Murray et al. | 549/510 |
| 5,760,251 | A | * | 6/1998 | Gao et al. | 549/510 |
| 5,808,113 | A | | 9/1998 | Murray et al. | |
| 6,531,611 | B2 | * | 3/2003 | Schloemer et al. | 548/215 |

FOREIGN PATENT DOCUMENTS

WO    97/07110    * 2/1997

OTHER PUBLICATIONS

European Search Report for Application No. 0374662, dated Jun. 29, 2005.
US 5,803,113, 09/1998, Murray et al. (withdrawn)

* cited by examiner

*Primary Examiner*—Margaret D. Seaman
*Assistant Examiner*—Niloofar Rahmani
(74) *Attorney, Agent, or Firm*—Alston & Bird LLP

(57) ABSTRACT

The invention provides methods and compositions for reductively deoxygenating an amide group at a C-3' position of a taxane molecule followed by subsequent intra-molecular acyl migration of an acyl group to the C-3' position.

43 Claims, No Drawings

CONVERSION OF TAXANE MOLECULES

CROSS REFERENCE TO RELATED APPLICATIONS

This application claims priority from U.S. Provisional Application Ser. No. 60/370,583, filed Apr. 5, 2002. This application is incorporated herein by reference in its entirety.

FIELD OF THE INVENTION

The invention relates generally to methods and compositions for converting a taxane molecule into another taxane molecule. More specifically, the invention relates to methods and compositions for reductively deoxygenating an amide group at a C-3' position of a taxane molecule followed by subsequent intra-molecular aryl migration of an acyl group to the C-3' position.

BACKGROUND OF THE INVENTION

Because of the promising clinical activity of certain taxanes (e.g., paclitaxel) against various types of cancer, there is an ongoing need for different methods for preparing paclitaxel and other taxane molecules, including paclitaxel derivatives and analogues. It is believed that the preparation of paclitaxel derivatives and analogues may result in the synthesis of compounds with comparable or greater potency, superior bioavailability, and/or fewer side effects than paclitaxel. Interconversion of one taxane molecule into another taxane molecule is one route to provide various paclitaxel derivatives and analogues for further study of their biological properties.

Murray et al. describe a process for converting taxol A, taxol B, and taxol C to taxol A or docetaxel (U.S. Pat. Nos. 5,679,807 and 5,808,113). The process generally includes reductive deoxygenation of the C-3' amide group of a fully protected taxane molecule using Schwartz's reagent to form an imine, followed by hydrolysis of the imine to a primary amine. Subsequent acylation of the primary amine with benzoyl chloride or tert-butyloxycarbonyl anhydride can produce taxol A or docetaxel, respectively.

In another example, Kingston et al. describe the conversion of cephalomannine into paclitaxel by substituting the 2-methyl-2-butenoyl group on the C-13 side chain of cephalomannine with a benzoyl group (U.S. Pat. No. 5,319,112). The methodology generally includes in sequential order: hydrogenation of the 2-methyl-2-butenoyl group, benzoylation of the C-2' hydroxyl group, protection of the C-7 hydroxyl group as its trichloroethyloxycarbonyl group, reaction of the C-3' amide functionality with oxalyl chloride followed by addition of water, reaction with diphenylcarbodiimide to create a free amine at the C-3' position followed by acyl migration of the benzoyl group from the C-2' hydroxyl group, and removal of the trichloroethyloxycarbonyl group.

However, there is still a need for more efficient and higher yielding synthetic methodologies for converting taxane molecules into other taxane molecules, which may be more potent anti-cancer compounds.

SUMMARY OF T INVENTION

It is an object of the invention to provide methods and compositions for the interconversion of a taxane molecule into another taxane molecule. More specifically, 2'-O acyl-protected taxane molecules can be efficiently converted to taxane molecules having a free C-2' hydroxyl group with the 2'-O acyl group migrating and ultimately coupling to the C-3' amino group.

In one embodiment, the invention provides a method of converting a taxane molecule having the formula:

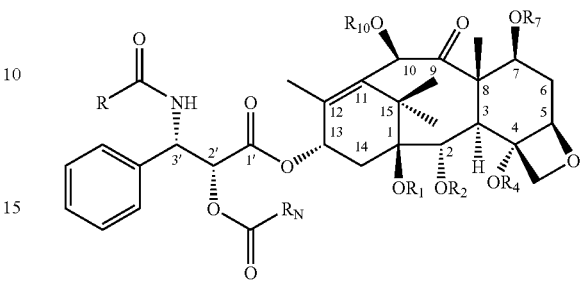

where $R_1$ is hydrogen, an alkyl group, an aryl group, an ester group, an ether group, or a hydroxyl protecting group; $R_2$ is hydrogen, an alkyl group, an aryl group, an ester group, an ether group, or a hydroxyl protecting group; $R_4$ is hydrogen, an alkyl group, an and group, an ester group, an ether group, or a hydroxyl protecting group; $R_7$ is hydrogen, an alkyl group, an aryl group, an ester group, an ether group, a glycoside group, an oxo-group, or a hydroxyl protecting group; $R_{10}$ is hydrogen, an alkyl group, an aryl group, an ester group, an ether group, or a hydroxyl protecting group; R is an alkoxy group, an alkyl group, an aryl group, an arylalkyl group, an ether group, heterocyclic group, or a vinyl group; and $R_N$ is an alkoxy group, an alkyl group, an aryl group, an arylalkyl group, an ether group, or a heterocyclic group, or a vinyl group;

to another taxane molecule having the formula:

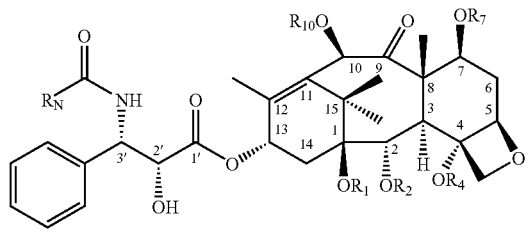

where $R_1$, $R_2$, $R_4$, $R_7$, $R_{10}$ and $R_N$ are as defined above.

The method generally includes the steps of reductively deoxygenating the taxane molecule to form an imine compound; hydrolyzing the imine compound to form a primary amine compound; and contacting the primary amine compound with a base to effect acyl migration. Preferably the interconversion of the taxane molecule occurs without isolation of one or more of the intermediates, i.e., the imine compound and the primary amine compound, thereby providing an efficient, cost effective synthetic methodology.

Preferred R groups are those of known taxane molecules and derivatives thereof, e.g., phenyl, 1-methyl-1-propenyl, n-pentyl, propyl, 1-methyl-propyl, benzyl, 2-furanyl, and tert-butoxy. Preferred $R_N$ groups are substituents of acyl groups, which after migration to the C-3' primary amine, define known taxane molecules and derivatives thereof. For example, preferred $R_N$ groups are phenyl, 1-methyl-1-propenyl, n-pentyl, propyl, 1-methyl-propyl, benzyl, 2-furanyl, and tert-butoxy. In addition, preferred taxane molecules include taxane molecules having the above-illustrated formula, where $R_1$ is hydrogen; $R_2$ is a benzoyl group; $R_4$ is an acetate group; $R_7$ is hydrogen; and $R_{10}$ is hydrogen or an acetate group.

The reductive deoxygenation preferably is carried out using a zirconium hydride compound such as zirconocene chloride hydride (bis(cyclopentadienyl)zirconium chloride hydride), commonly known as Schwartz's reagent. Preferably, about 3 or more molar equivalents of zirconocene chloride hydride are used and/or the reaction temperature is maintained at less than about 15° C.

Following conversion to the imine compound, an acid preferably is used to hydrolyze the imine compound to provide a primary amine at the C-3' position. Any common non-oxidizing acid may be used. Examples of acids include, among others, acetic acid, hydrobromic acid, hydrochloric acid, and sulfuric acid. Subsequently, acyl migration of a 2'-O acyl group provides the end product. A preferred base to effect acyl migration is a trialkylamine such as triethylamine.

The foregoing, and other features and advantages of the invention, as well as the invention itself, will be more fully understood from the description, figures, and claims which follow.

DETAILED DESCRIPTION OF THE INVENTION

The invention is based, in part, on the discovery of an efficient synthetic route for the interconversion of taxane molecules that may be realized using reductive deoxygenation, hydrolysis, and subsequent acyl migration. In particular, the method of the invention has utility in the transformation of mixtures of taxane molecules into one specific taxane molecule.

As used herein, an "acyl group" means a linear, branched, or cyclic substituent having a carbonyl group which is attached to either an oxygen atom, e.g., of a hydroxyl group, or a nitrogen atom, e.g., of an amino group. An acyl group can include an alkoxy group, an alkyl group, an aryl group, an arylalkyl group, an ester group, an ether group, a heterocyclic group, a vinyl group, and combination thereof. An acyl group also may be substituted with substituents such as alkanoyloxy groups, alkenyl groups, alkylsilyl groups, alkylsulfonyl groups, alkylsulfoxy groups, alkylthio groups, alkynyl groups, amino groups such as mono- and di-alkylamino groups and mono- and di-arylamino groups, amide groups, carboxy groups, carboxyalkoxy groups, carboxyamide groups, carboxylate groups, haloalkyl groups, halogens, hydroxyl groups, nitrile groups, nitro groups, phosphate groups, siloxy groups, sulfate groups, sulfonamide groups, sulfonyloxy groups, and combinations of these. It should be understood that an acyl group also can be an amino protecting group or a hydroxyl protecting group. As a hydroxyl protecting group, an acyl group may form an ester. As an amino protecting group, an acyl group may form an amide or a carbamate. Examples of acyl groups include, but are not limited to, alkylacyl groups, arylacyl groups, aryl alkyl groups, and vinylacyl groups. Preferred acyl groups are benzoyl, ethanoyl, tigloyl or 2-methyl-2-butenoyl, 2-methyl-1-propenoyl, hexanoyl, butyryl, 2-methylbutyryl, phenylacetyl, propanoyl, furoyl, and tert-butyloxycarbonyl.

As used herein, an "alkoxy group" means a linear, branched, or cyclic saturated hydrocarbon attached to an oxygen atom. Preferably, an alkoxy group has between one and six carbon atoms. An alkoxy group also refers to substituted alkoxy groups, which may include substituents such as alkanoyloxy groups, alkenyl groups, alkyl groups, alkylsilyl groups, alkylsulfonyl groups, alkylsulfoxy groups, alkylthio groups, alkynyl groups, amino groups such as mono- and di-alkylamino groups and mono- and di-arylamino groups, amide groups, aryl groups, arylalkyl groups, carboxy groups, carboxyalkoxy groups, carboxyamide groups, carboxylate groups, haloalkyl groups, halogens, hydroxyl groups, nitrile groups, nitro groups, phosphate groups, siloxy groups, sulfate groups, sulfonamide groups, sulfonyloxy groups, and combinations of these. Preferred examples of alkoxy groups include, among others, methoxy, ethoxy, propoxy, cyclopropoxy, isopropoxy, n-butoxy, isobutoxy, sec-butoxy, tert-butoxy, cyclobutoxy, pentoxy, isopentoxy, neo-pentoxy, cyclopentoxy, hexoxy, and cyclohexoxy.

As used herein, an "alkyl group" means a linear, branched, or cyclic saturated hydrocarbon. Preferably, an alkyl group has between one and six carbon atoms. An alkyl group also refers to substituted alkyl groups, which may include substituents such as alkanoyloxy groups, alkenyl groups, alky groups, alkylsilyl groups, alkylsulfonyl groups, alkylsulfoxy groups, alkylthio groups, alkynyl groups, amino groups such as mono- and di-alkylamino groups and mono- and di-arylamino groups, amide groups, aryl groups, arylalkyl groups, carboxy groups, carboxyalkoxy groups, carboxyamide groups, carboxylate groups, haloalkyl groups, halogens, hydroxyl groups, nitrile groups, nitro groups, phosphate groups, siloxy groups, sulfate groups, sulfonamide groups, sulfonyloxy groups, and combinations of these. Preferred substituents are alkoxy groups, amino groups such as dialkylamino groups, diarylamino groups, carboxylic acid-containing groups, haloalkyl groups, halogens, hydroxyl groups, nitrile groups, nitro groups, and sulfonic acid groups. Examples of preferred alkyl groups include, but are not limited to, methyl, ethyl, propyl, isopropyl, cyclopropyl, n-butyl, isobutyl, sec-butyl, tert-butyl, cyclobutyl, pentyl, isopentyl, neo-pentyl, 1-ethylpropyl, cyclopentyl, hexyl, and cyclohexyl.

As used herein, an "amino protecting group" means a substituent of an amino group that is employed to block or protect the amino functionality, often while reacting other functional groups on the molecule. Example of amino protecting groups are well known in the art and are described in J. W. Barton, "Protecting Groups in Organic Chemistry," J. G. W. McOmie, ed., Plenum Press, New York, N.Y., 1973, and in T. W. Greene and P. G. M. Wuts, "Protective Groups in Organic Synthesis," John Wiley & Sons, New York, N.Y., 1999. It should be understood that an amino protecting group may remain on an end product.

As used herein, an "aryl group" means a phenyl group or naphthyl group, which is optionally substituted. Examples of substituents on aryl groups include, but are not limited to, alkanoyloxy groups, alkenyl groups, alkoxy groups, alkylsilyl groups, alkylsulfonyl groups, alkylsulfoxy groups, alkylthio groups, alkynyl groups, amino groups such as mono- and di-alkylamino groups and mono- and di-arylamino groups, amide groups, aryl groups, arylalkyl groups, carboxy groups, carboxyalkoxy groups, carboxyamide groups, carboxylate groups, haloalkyl groups, halogens, hydroxyl groups, nitrile groups, nitro groups, phosphate groups, siloxy groups, sulfate groups, sulfonamide groups, sulfonyloxy groups, and combinations of these. Preferred substituents are alkoxy groups, alkyl groups, amino groups such as dialkylamino groups and diarylamino groups, carboxylic acid-containing groups, haloalkyl groups, halogens, hydroxyl groups, nitrile groups, nitro groups, and sulfonic acid groups.

As used herein, an "arylalkyl group" means an aryl group attached to an alkyl group. An example of an arylalkyl group is a benzyl group.

As used herein, a "basic baccatin III structure" means a compound having the formula:

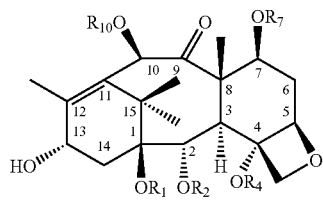

where each of $R_1$, $R_2$, $R_4$, $R_7$, and $R_{10}$ independently is hydrogen, an alkyl group, an acyl group, an aryl group, an arylalkyl group, a vinyl group, an ether group, an ester group, a glycoside group, an oxo group, or a hydroxyl protecting group. Included within the definition of a basic baccatin III structure is baccatin III, which has the formula:

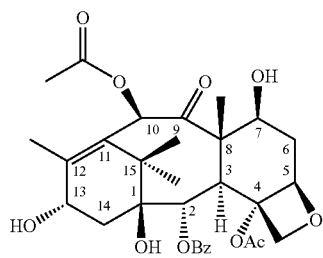

and 10-deacetylbaccatin III, which has the formula:

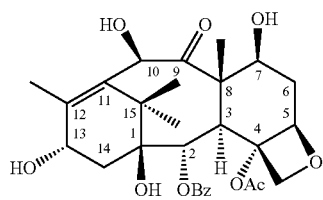

where Ac is an acetyl or acetate group ($CH_3C(O)$—), and Bz is a benzoyl group (PhC(O)— or $C_6H_5C(O)$—).

As used herein, an "ester group" means a linear, branched, or cyclic substituent having an ester functionality, i.e., —C(O)O—. Examples of ester groups include acyl groups such as ethanoyl and propanoyl, which are bound to a hydroxyl group.

As used herein, an "ether group" means a linear, branched, or cyclic substituent having an ether functionality, i.e., —COC—. An examples of an ether group includes, but is not limited to, $HOCH_2CH_2OC(CH_2OH)H$—.

As used herein, a "glycoside group" or a "glycosyl group" means any of a number of sugar derivatives that contain a non-sugar group bonded to an oxygen or nitrogen atom and that on hydrolysis yield a sugar such as glucose. An example of a preferred gylcosyl group is xylosyl.

As used herein, a "halogen" means fluorine, chlorine, bromine, and/or iodide.

As used herein, a "heterocyclic group" is a saturated, unsaturated, or aromatic cyclic compound that contains at least one atom other than carbon, e.g., oxygen, nitrogen, or sulfur, in a ring. Examples of heterocyclic groups include furyls such as 2-furan, morpholino, piperadino, piperazino, N-methylpiperazino, pyrrollyl, pyridyl, and thiophene.

As used herein, a "hydroxyl protecting group" means a substituent of a hydroxyl group that is employed to block or protect the hydroxyl functionality, often while reacting to other functional groups on the molecule. Examples of hydroxyl protecting groups are well known in the art and are described in J. W. Barton, "Protecting Groups in Organic Chemistry," J. G. W. McOmie, ed., Plenum Press, New York, N.Y., 1973, and in T. W. Greene and P. G. M. Wuts, "Protective Groups in Organic Synthesis," John Wiley & Sons, New York, N.Y., 1999. It should be understood that a hydroxyl protecting group may remain on an end product. Examples of preferred hydroxyl protecting groups include, among others, acyl groups such as acetate (Ac) and benzoyl (Bz), trimethylsilyl (TMS), triethylsilyl (TES), trichloroethoxycarbonyl, and 2,2,2-trichloroethyloxycarbonyl ($Cl_3CH_2OC(O)$—).

As used herein, an "oxo-group" means a substituent derived from the oxidation of a glycoside group such as a xyloside as described in U.S. Pat. No. 5,356,928.

As used herein, "taxane molecule" means a molecule that contains a basic baccatin III structure with a (2R,3S)—$C_6H_5CH(Rx)CH(OH)C(O)$— group forming an ester with the hydroxyl group located at the C-13 position of the basic baccatin III structure. The group represented by Rx can be an amino group, a salt of an amino group (e.g., an ammonium salt), an amino group which is protected with an amino protecting group, or a substituent which may be converted into an amino group. Various isomers, homologues, and analogues of the basic baccatin III structure, and of the (2R,3S)—$C_6H_5CH(Rx)CH(OH)C(O)$— group also are included in the definition of a taxane molecule. For example, a 10-deacetylbaccatin m structure is contemplated within the scope of a taxane molecule. Included within the definition of a taxane molecule are taxol A (paclitaxel), taxol B (cephalomannine), taxol C, taxol D, taxol E, taxol F, taxol G, docetaxel (TAXOTERE®), and nonataxel (see, e.g., Table 1).

As used herein, a "vinyl group" means a linear or branched substituent having a carbon-carbon double bond. Examples of vinyl groups include, but are not limited to, 1-methyl-1-propenyl ($CH_3CH=C(CH_3)$—), and 2-methyl-1-propenyl (($CH_3)_2C=CH$—).

TABLE 1
Examples Of $R_N$ Groups In Known Taxane Molecules
| Taxane | $R_N$ | Molecular Structure |
|---|---|---|
| Taxol A (paclitaxel) | 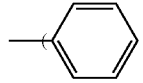 | 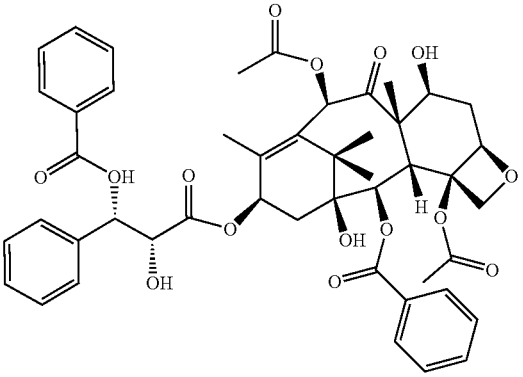 |
| Taxol B (cephalomannine) | 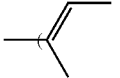 | 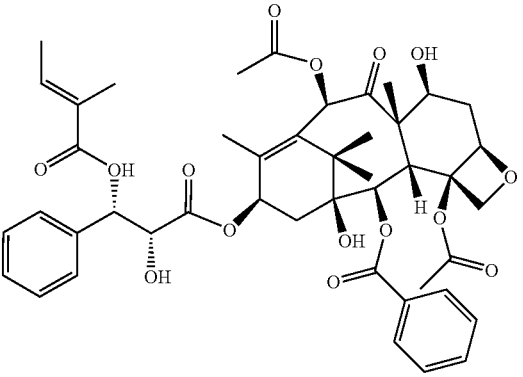 |
| Taxol C | 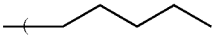 | 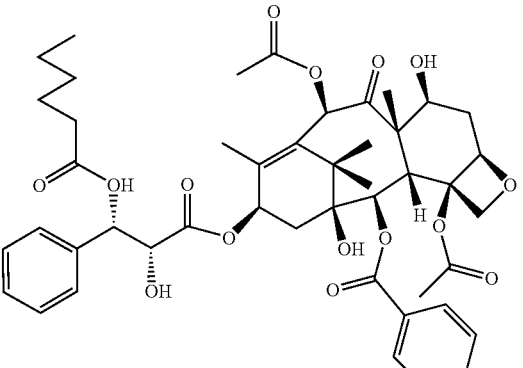 |
| Taxol D |  | 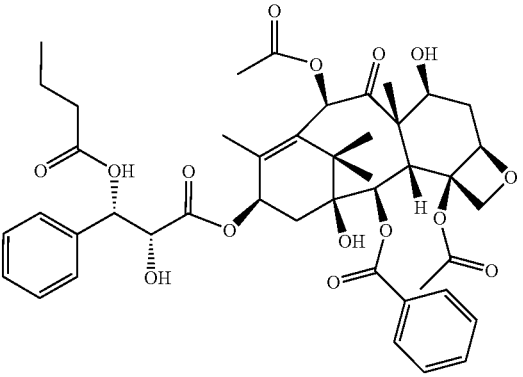 |

TABLE 1-continued
Examples Of $R_N$ Groups In Known Taxane Molecules
| Taxane | $R_N$ | Molecular Structure |
|---|---|---|
| Taxol E | 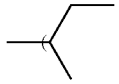 | 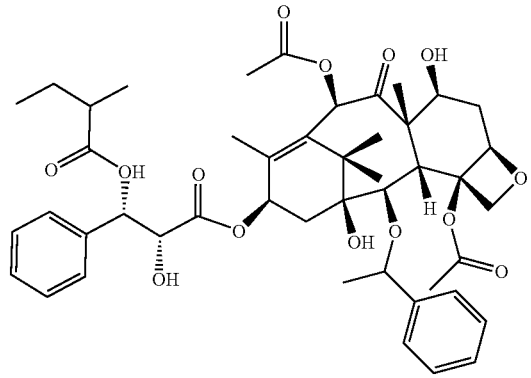 |
| Taxol F | 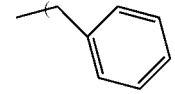 | 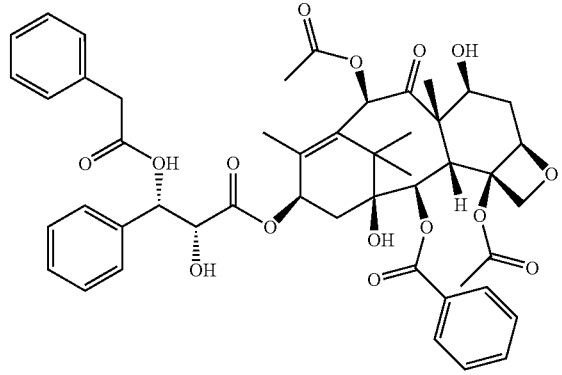 |
| Taxol G | 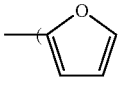 | 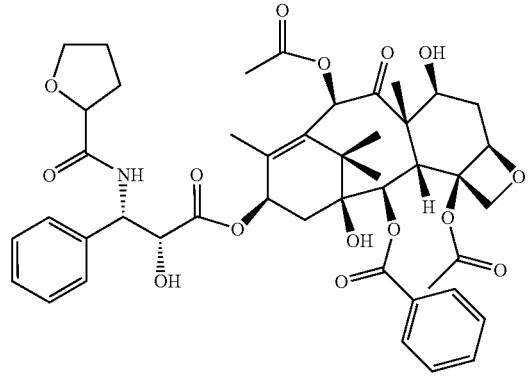 |
| Docetaxel (Taxotere ®) | 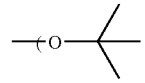 | 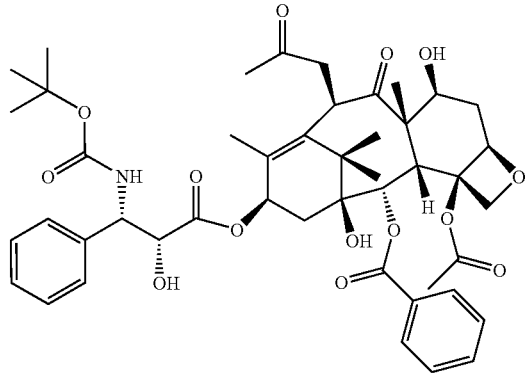 |

TABLE 1-continued

Examples Of $R_N$ Groups In Known Taxane Molecules

| Taxane | $R_N$ | Molecular Structure |
|---|---|---|
| Nonataxel | | 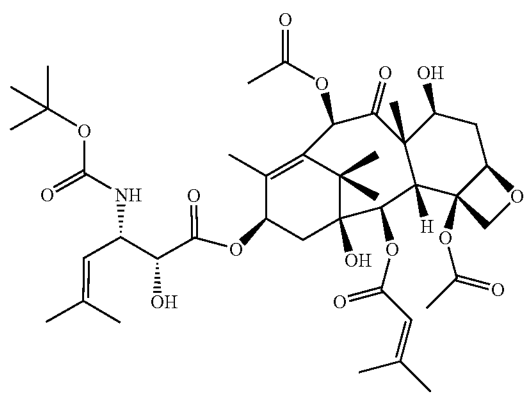 |

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of the recited processing steps. Further, it should be understood that the order of steps or order for performing certain actions are immaterial so long as the invention remains operable. Moreover, two or more steps or actions may be conducted simultaneously.

In one alternative embodiment, the present invention relates to a method of converting a taxane molecule having a C-2' hydroxyl group. The hydroxyl group may be acylated according to the processes described in U.S. Pat. Appl. No 60/370,252, filed Apr. 5, 2002. This application is incorporated herein by reference. The C-2' acylated taxane may or may not be purified or isolated before reductively deoxygenating the taxane molecule. In another embodiment, the invention relates to a method of reductively deoxygenating a C-3' amide functionality of a taxane molecule followed by hydrolysis and subsequent acyl migration of an acyl group on the C-2' hydroxyl group. Here, the hydroxyl group may be acylated according to the process described in the '252 application cited above.

The method of the present invention generally includes the steps of reductively deoxygenating a taxane molecule to form an imine compound; hydrolyzing the imine compound to form a primary amine compound; and contacting the primary amine compound with a base to effect acyl migration. Preferably the interconversion of the taxane molecule occurs without isolation of the intermediates, i.e., the imine compound and the primary amine compound, thereby providing an efficient, cost effective methodology for the interconversion of taxane molecules.

In a particular embodiment, the invention provides a method for converting a taxane molecule having the formula:

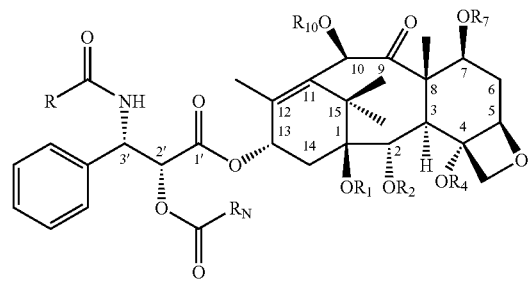

where each of $R_1$, $R_2$, $R_4$, $R_7$, and $R_{10}$ independently is hydrogen, an alkyl group, an acyl group, an aryl group, arylalkyl group, a vinyl group, an ether group, an ester group, a glycoside group, an oxo-group, or a hydroxyl protecting group, and each of R and $R_N$ independently is hydrogen, an alkoxy group, an alkyl group; an aryl group, an arylalkyl group, an ether group, heterocyclic group, or a vinyl group to another taxane molecule having the formula:

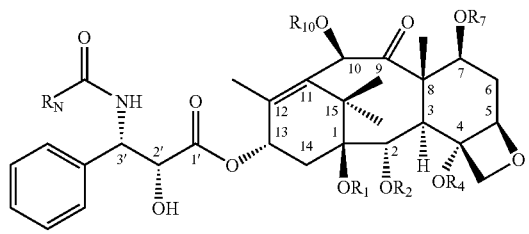

where $R_1$, $R_2$, $R_4$, $R_7$, $R_{10}$ and $R_n$ are as defined above.

Preferably $R_1$, is hydrogen; $R_2$, is hydrogen, an acyl group, or a hydroxyl protecting group; $R_4$ is an acetat4e group; $R_7$ is hydrogen, an aryl group, an aryl group, an ester group, an ether group, a glycoside group, an oxo-group, or a hydroxyl protecting group; $R_{10}$ is hydrogen, an alkyl group, an aryl group, an ester group, an ether group, or a hydroxyl protecting group; R is an alkoxy group, an alkyl group, an aryl group, an arylalkyl group, heterocyclic group, or a vinyl group.

Preferred starting materials include taxane molecules having the above-illustrated formula, where $R_1$ is hydrogen; $R_2$ is a benzoyl group; $R_4$ is an acetate group; $R_7$ is hydrogen; and $R_{10}$ is hydrogen; and where $R_1$ is hydrogen; $R_2$ is a benzoyl group; $R_4$ is an acetate group; $R_7$ is hydrogen; and $R_{10}$ is an acetate group; and each of R and $R_N$ is a group corresponding to known taxol molecule or derivative thereof, e.g., phenyl, 1-methyl-1-propenyl, n-pentyl, propyl, 1-methyl-propyl, benzyl, 2-furanyl, and tert-butoxy. Thus, among preferred starting materials for the interconverion reactions of the invention are the taxane molecules depicted in Table 1 where the C-2' hydroxyl group is protected with benzoyl, 2-methyl-2-butenoyl, hexanoyl, butyryl, 2-methyl-butyryl, phenylacetyl, furoyl, or tert-butyloxycarbonyl. Other examples of $R_N$ groups include, among others, acetyl ($CH_3C(O)$—), $HOC(O)$—, $CH_3OC(O)$—, $CH_3CH(OH)C(OH)(CH_3)$—, and $PhNHC(O)$—.

A more preferred starting material of the interconversion reaction of the invention is a taxane molecule having the formula:

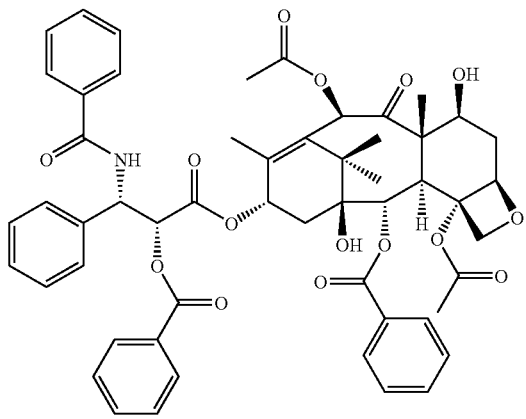

Another preferred starting material of the interconversion reaction of the invention is a taxane molecule having the formula:

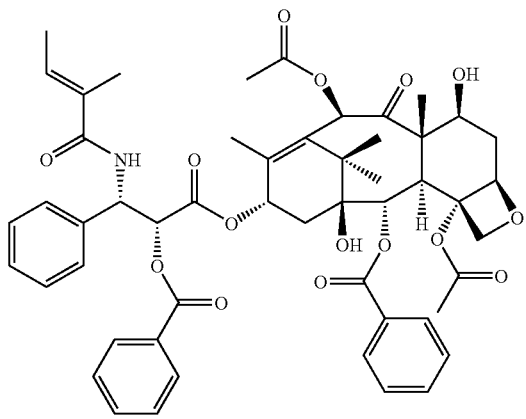

The reductive deoxygenation may be effected using reagents known in the art. In one alternative embodiment, this reaction may be achieved by contacting the taxane molecule with a transition metal containing compound or transition metal reducing agent. The reductive dehydrogenation preferably is carried out using a zirconium hydride compound such as zirconocene chloride hydride (bis(cyclopentadieny) zirconium chloride hydride), also known as Schwartz's reagents. Other transition metal containing compounds or transition metal reducing agents, include, but are not limited to, titanium-containing reducing agents, hafnium-containing reducing agents, niobium-containing reducing agents, and molybdenum-containing reducing agents may be used. Analogues and derivatives of Schwartz's reagent may also be used. In one alternative embodiment, the amount of Schwartz's reagent used can vary from about 0.1 molar equivalent up to about 10 molar equivalents per mole of starting material, preferably at about 2 or more molar equivalents may be used. More preferably, about 3 or more molar equivalents of Schwartz's reagent are used, with Schwartz's reagent being added as a slurry in an appropriate solvent. Preferably, the solvent is anhydrous. Tetrahydrofuran is a preferred solvent.

The reductive deoxygenation preferably is carried out in an inert environment, e.g., under a nitrogen or argon atmosphere. In an alternative embodiment, the solution of the starting material(s) is a solvent. The solvent may be agitated and cooled below ambient temperature prior to the addition of Schwartz's reagent. The pre-reaction solution temperature is preferably less than about 15° C., and more preferably less than about 10° C.

The slurry of Schwartz's reagent is added to the cooled solution containing the starting material(s) while maintaining agitation of the solution. After addition of Schwartz's reagent, hydrogen gas is generated and the reaction solution will warm slightly as the reaction is mildly exothermic. Following complete addition of the Schwartz's reagent, agitation of the reaction solution usually continues at a reduced temperature until the reaction is deemed complete. The reaction time typically is about 1–4 hours.

As with most chemical reactions, its progress may be monitored to completeness, e.g., using thin layer chromatography (TLC) or high performance liquid chromatography (HPLC). A reaction preferably is deemed complete when the starting material(s) are no longer present Subsequent to completion of the reductive deoxygenation reaction, most of the transition metal and or transition metal by-products may be removed before proceeding with the next reaction. For example, in one alternative embodiment, all or substantially all of the transition metal or metal by-products may be removed such that the resultant mixture comprises less than 10,000 parts/million, preferably less than 5,000 parts/million, or more preferably less than 1000 parts per million of transition metal or transition metal by-products. For the present invention, removal of the transition metal or any metal by-products is optional. It is understood that the removal of transition metal or any transition metal by-products may be performed separately or in conjunction with any other step described herein. Also, such removal step may be performed at various times during the process of the present invention. Techniques for removing transition metal compounds or transition metal by-products are known in the art, including, but not limited to, complexation, precipitation, filtration, chelation, centrifugation, electrochemical methodology, chromatography, or any combination thereof. In one alternative embodiment, a chelating agent comprising a chelating agent effective to chelate a transition metal may be used to remove the transition metal compound or transition metal by-product. Such chelating agents may include, but are not limited to, ethylene diamine tetra acetic acid (EDTA), ethylene glycol (bis) aminoethyl ether tetra acetic acid (EGTA), 1,2-bis-(o-aminophenoxy)ethane, N,N,N',N'-tetra-acetic acid (BAPTA), N,N,N',N'-tetrakis-(2-pyridylmethyl)ethylenediamine (TPEN), nitrilotriacetic acid, TIRON®, and analogues and derivatives thereof. In one alternative embodiment, the cooled reductive deoxygenation reaction solution is added to an excess of N,N-bis(2-hydroxyethyl)glycine (bicine) as an aqueous solution while maintaining the solution at an ambient temperature. About 2 or more equivalents of bicine preferably may be used based on the amount of transition metal present. Subsequently the reaction is appropriately worked-up, which may include additional treatment of the original reductive deoxygenation reaction solution with additional aqueous bicine solution.

After the reductive deoxygenation reaction, the starting taxane molecule is converted to an imine compound, i.e., the C-3' amide group of the taxane molecule is converted to an imine (—N=CH—) group. More specifically, the imine compound generally has the formula:

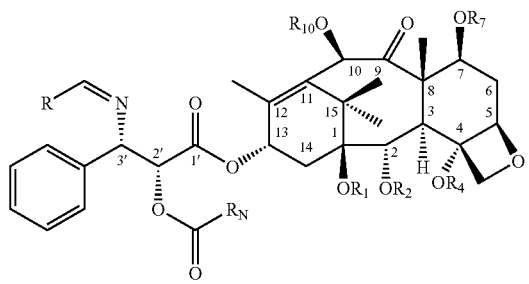

where $R_1$, $R_2$, $R_4$, $R_7$, $R_{10}$, R, and $R_N$ are as defined above.

Following conversion to an imine compound, hydrolysis of the imine functionality produces a free amine, i.e., a primary amine. at the C-3' position. Any common non-oxidizing acid may be used to effect the hydrolysis of the imine compound. Examples of acids include, among others, acetic acid, hydrobromic acid, hydrochloric acid, or preferably sulfuric acid. The acid may be aqueous and/or in solution with a protic solvent, e.g. ethanol and/or methanol. In theory, about 2 or more molar equivalents of acid should be used per mole of imine.

Hydrolysis of the imine compound may be carried out at about ambient temperature. Also, hydrolysis may be carried out on an isolated and/or purified imine compound. Preferably, an aqueous solution of an acid is added directly to the organic layer (organic phase) of the reductive deoxygenation reaction mixture. After the hydrolysis is complete, a base, e.g., an aqueous solution of sodium carbonate, may be added to neutralize the acidic hydrolysis reaction.

Because acids often are used to remove various protecting groups utilized in synthetic reaction schemes, care should be taken in the selection of an appropriate hydrolysis reagent to avoid unwanted removal of protecting groups which may be present on the taxane molecule. However, it may be desirable to remove certain protecting groups on a taxane molecule to facilitate conversion of a "protected" taxane molecule to a known taxol derivative, e.g., removal of a silyl protecting group from the C-7 and/or C-10 hydroxyl groups. Accordingly, if an acid is to perform additional functions in the reaction, the amount of acid used in the reaction should be appropriately adjusted.

After hydrolysis of the imine functionality, the starting taxane molecule (and the imine compound) are converted to a primary amine compound, i.e., the C-3' amide group of the taxane molecule or the C-3' imine group of the imine compound is converted to a primary amine, i.e., —NH$_2$. More specifically, the primary amine compound generally has the formula:

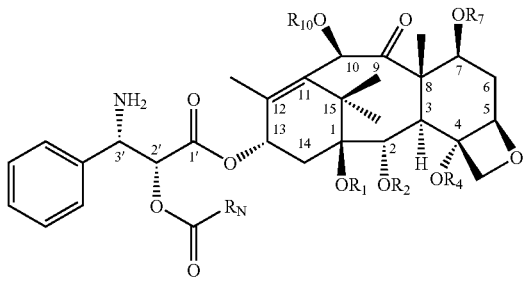

where $R_1$, $R_2$, $R_4$, $R_7$, $R_{10}$, and $R_N$ are as defined above.

Finally, the primary amine compound is exposed to a basic environment to effect acyl migration of the 2'-O acyl group to the C-3' primary amine. Any base known in the art to facilitate acyl migration may be used provided it does not adversely affect other functionality present on the taxane molecule, i.e; the primary amine compound, and/or produce by-products. Examples of bases suitable for effecting acyl migration include, but are not limited to, trialkylamines, pyridine, substituted pyridines, sodium bicarbonate, sodium carbonate, and potassium carbonate. A preferred base is triethylamine.

In practice, the base may be added to a solution of isolated and/or purified primary amine compound. Preferably, the base is added directly to the organic layer (organic phase) resulting from hydrolysis of the imine compound. In the case of the latter, it may be desirable also to add a zirconium chelator along with the base to chelate and/or remove any additional traces of zirconium. For example, 2-aminobenzoic acid (anthranilic acid) preferably is added along with a trialkylamine. The reaction typically is conducted at about ambient temperature with some form of agitation, e.g., stirring.

When the reaction is deemed complete as determined by HPLC analysis, the reaction is worked-up using known procedures, e.g., standard neutralization and washing steps. After an appropriate work-up, the organic layer typically is dried using conventional drying reagents such as magnesium sulfate.

After work-up of the acyl migration reaction, the end product taxane molecule usually is isolated. A number of isolation techniques may be used, e.g., evaporation of the organic solvent under reduced pressure to provide an amorphous solid. However, the dried organic layer resulting from the work-up of the acyl migration reaction preferably is added to an anti-solvent for taxane molecules such as hexane or heptane. Subsequent to precipitation, the solid end product taxane molecule can be collected by filtration then dried under reduced pressure and/or elevated temperature, for example.

After the desired taxane mixture is obtained, it may be crystallized. Depending on the desired purity of the end product taxane molecule, the resulting taxane mixture may be recrystallized one or more times. Crystallization and recrystallization may be conducted using a binary or ternary solvent system, i.e., at least one solubilizing solvent and at least one anti-solvent. Examples of solubilizing solvents include, among others, acetone, methyl tert-butyl ether, methylene chloride, trifluorotoluene, THF, methanol, ethanol, isopropyl alcohol, and acetonitrile. Examples of anti-solvents include, for example, hydrocarbon solvents such as hexane and heptane, as well as water. In most cases, the solubilizing solvent and the anti-solvent are miscible in the ratios used. Examples of solvent systems useful with taxane molecules include, among others, acetone/hexane, methanol/water and methylene chloride/hexane. Methylene chloride/hexane is preferred for the C-2' acylated taxane. Acetone/hexane and methanol/water are preferred for taxol A.

The end product and/or isolated intermediates may be analyzed using analytical techniques known in the art such as infrared (IR) spectroscopy, nuclear magnetic resonance (NMR) spectroscopy, e.g., $^1$H-N and $^{13}$C-NMR, high performance liquid chromatography (HPLC), e.g., reversed phase HPLC, and/or mass spectrometry (MS), e.g., electrospray ionization MS (ES MS) and matrix-assisted laser adsorption ionization MS (MALDI-MS). Combinations of these techniques also may be used, e.g., HPLC-MS.

In an embodiment of the above-described methodology, the invention is directed to methods of interconverting mixtures of taxane molecules, e.g., from biomass or biomass extracts, to a particular taxane molecule, e.g., paclitaxel. The methodology for interconversion of mixtures of taxane molecules into a specific taxane molecule generally is the same as for the interconversion of a single taxane molecule into another single taxane molecule.

The invention is further illustrated by the following non-limiting examples:

EXAMPLES

Anthranilic acid (2-aminobenzoic acid), ethyl acetate (EtOAc), heptane, N,N-bis(2-hydroxyethyl)glycine (bicine), magnesium sulfate ($MgSO_4$), sodium carbonate ($Na_2CO_3$), sulfuric acid ($H_2SO_4$), tetrahydrofuran (THF), and triethylamine ($Et_3N$) were purchased from Sigma-Aldrich Co. (Milwaukee,:Wis.). Zirconocene chloride hydride (Schwartz's reagent) was purchased from Soltec Ventures (Beverly, Mass.).

The HPLC assay used is as follows: Column: Waters XTerra RP18, 50×:4.6 mm, 3.5 micron. Flow Rate: 2.0 mL/min. Gradient: All solvents contain 0.05% formic acid. Start at 5%/95% water/acetonitrile ($CH_3CN$), at 0.75 minutes step to 30%/70% water/$CH_3CN$ and begin a linear gradient to 80%120% water/$CH_3CN$ at 6 minutes, then hold until 7.5 minutes. Re-equilibration is with 5%/95% water/$CH_3CN$ for 3 minutes. Detection: 227 and 254 run.

Conversion of 2'-O Benzoyl Taxane Molecules to Paclitaxel

Reductive Deoxygenation

One kilogram of a mixture of 2'-O benzoyl taxane molecules (including taxol A, taxol B, taxol C, taxol D, taxol E, taxol F, and taxol G) was dissolved in 3.0 L anhydrous THF. The solution was added through a 1.0-micron in-line filter to a jacketed reaction vessel under an inert environment The solution was cooled to 0–10° C. with agitation. A previously-prepared slurry consisting of 0.94 kg of Schwartz's reagent (3.2 eq.) and 2.0 L of anhydrous THF was added to the reaction solution over about 5 minutes with agitation.

This reaction was mildly exothermic and generated hydrogen ($H_2$) gas. The reaction was agitated at 0–10° C. until the reaction end-point was determined by the HPLC assay.

Zr Removal

When the reaction was deemed complete, the reaction mixture was added to 3.66 L of 2 M aqueous bicine solution (2.0 eq. based on Zr). The reaction vessel was rinsed with 1.7 L of THF, which also was added to the bicine solution. The bicine solution was stirred at 15–20° C. for about 30 minutes. Subsequently, agitation was stopped for about 15 minutes and the lower aqueous layer was transferred to another vessel. To the aqueous layer was added 5.0 L of ethyl acetate and the solution was agitated for about 10 minutes. Agitation was stopped, for about 15 minutes allowing the layers to separate and the lower aqueous layer was removed and discarded. To the original THF solution was added another 3.66 L of 2 M aqueous bicine solution along with 1.0 L of brine solution. The total solution was agitated at 15–20° C. for about 30 minutes. Agitation was stopped and the lower aqueous layer was transferred to the vessel containing the ethyl acetate. This solution was then agitated for about 15 minutes and the lower aqueous layer was discarded. The ethyl acetate was then transferred to the THF solution.

Imine Hydrolysis

With stirring at 20–25° C., 0.4 L of a 10% aqueous $H_2SO_4$ solution was added to the combined organic layers and the batch stirred for about 60 minutes. Then 1.0 L of a 2 M $Na_2CO_3$ solution was added with stirring for about 15 minutes. Agitation was stopped for about 15 minutes and the lower aqueous layer was disposed of.

Benzoyl Migration and Product Recovery

To the organic layer was added 0.25 kg of solid anthranilic acid and 250 mL triethylamine. The batch was agitated until the reaction end-point was determined by the HPLC assay. When the reaction was deemed complete, a total of 3.65 L of IM aqueous $Na_2CO_3$ solution was added with stirring for about 45 minutes at 20–25° C. Agitation was stopped for 15 minutes and the lower aqueous layer was discarded. Subsequently; 2.0 L of a saturated brine solution was added to the batch and stirred for about 15 minutes at 20–25° C. Stirring was stopped and the lower aqueous layer was discarded. To the batch was added 0.67 kg of magnesium sulfate with agitation for about 30 minutes. The 30 $MgSO_4$ was filtered off and the solution was added to a total of 80.0 L heptane with stirring over about 30 minutes, which resulted in precipitation. The off-white solid precipitate was filtered through a plate filter under vacuum and the solids were washed with 10.0 L of heptane. The solids were dried under vacuum at 40–50° C. for about 48 hours. The resulting mass contained about 65–75% paclitaxel.

Incorporation by Reference

The content of each of the patent and non-patent documents referred to herein is expressly incorporated herein by reference.

Equivalents

The invention may be embodied in other specific forms without departing form the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

Also, the invention may suitably comprise, consist of or consist essentially of the elements or process steps described herein. Further, the invention described herein suitably may be practiced in the absence of any element or process step which is or is not disclosed herein.

What is claimed is:

1. A method of converting a taxane molecule having the formula:

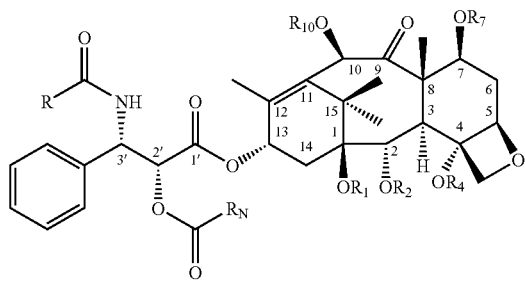

wherein
- $R_1$ is hydrogen, an alkyl group, an aryl group, an ester group, an ether group, or a hydroxyl protecting group;
- $R_2$ is hydrogen, an alkyl group, an aryl group, an ester group, an ether group, or a hydroxyl protecting group;
- $R_4$ is hydrogen, an alkyl group, an aryl group, an ester group, an ether group, or a hydroxyl protecting group;
- $R_7$ is hydrogen, an alkyl group, an aryl group, an ester group, an ether group, a glycoside group, an oxo-group, or a hydroxyl protecting group;
- $R_{10}$ is hydrogen, an alkyl group, an aryl group, an ester group, an ether group, or a hydroxyl protecting group;
- R is an alkoxy group, an alkyl group, an aryl group, an arylalkyl group, an ether group, heterocyclic group, or a vinyl group; and
- $R_N$ is an alkoxy group, an alkyl group, an aryl group, an arylalkyl group, an ether group, or a heterocyclic group, or a vinyl group;

the method comprising the steps of:
reductively deoxygenating the C-3' amide group on the taxane molecule to form an a C-3' imine compound;
hydrolyzing the imine compound to form a primary amine compound; and
treating the primary amine compound with a hindered base capable of effecting acyl migration to form another taxane molecule having the formula:

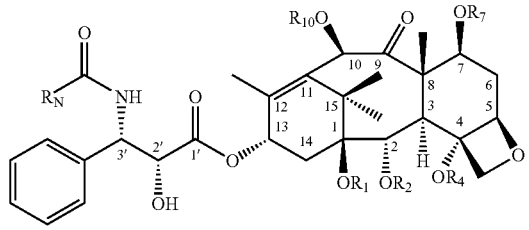

wherein
$R_1$, $R_2$, $R_4$, $R_7$, $R_{10}$, and $R_N$ are as defined above.

2. The method of claim 1 wherein the step of reductively deoxygenating the C-3' amide group on the taxane compound comprises contacting the taxane compound with a transition metal reducing agent.

3. The method of claim 2, wherein the transition metal reducing agent is Schwartz's reagent (zirconocene chloride hydride).

4. The method of claim 2, wherein the transition metal reducing agent is an analogue or derivative of Schwartz's reagent.

5. The method of claim 2, wherein the transition metal reducing agent is selected from the group consisting of titanium-containing reducing agents, hafnium-containing reducing agents, niobium-containing reducing agents, and molybdenum-containing reducing agents.

6. The method of claim 1 wherein the step of hydrolyzing the imine compound comprises contacting the imine compound with an acid.

7. The method of claim 6 wherein the acid is sulfuric acid.

8. The method of claim 1 wherein the step of treating the primary amine compound with a base comprises treating the primary amine compound with triethylamine.

9. The method of claim 1 wherein the step of treating the primary amine compound with a base comprises treating the primary amine compound with triethylamine and anthranilic acid.

10. The method of claim 1, further comprises the step of chelating the transition metal reducing agent or by-products thereof by adding a chelating agent.

11. The method of claim 1, wherein the chelating step comprises chelating the transition metal reducing agent or by-products thereof with a zirconium chelator.

12. The method of claim 11, wherein the chelating step comprises chelating the transition metal reducing agent or by-products thereof with N,N-bis(2-hydroxyethyl) glycine (bicine).

13. The method of claim 11, wherein the chelating step comprises chelating the transition metal reducing agent or by-products thereof with an agent comprising a chelating agent selected from the group consisting of ethylene diamine tetra acetic acid (EDTA), ethylene glycol (bis) aminoethyl ether tetra acetic acid (EGTA), 1,2-bis-(o-aminophenoxy) ethane-N,N,N',N'-tetra-acetic acid (BAPTA), N,N,N',N'-tetrakis-(2-pyridylmethyl) ethylenediamine (TPEN), nitrilotriacetic acid, TIRON® and analogues and derivatives thereof.

14. The method of claim 1 wherein the imine compound and the primary amine compound are not isolated prior to the next step.

15. The method of claim 1 wherein $R_N$ is phenyl, 1-methyl-1-propenyl, n-pentyl, propyl, 1-methyl-propyl, benzyl, 2-furanyl, ortert-butoxy.

16. A method of converting a taxane molecule having the formula:

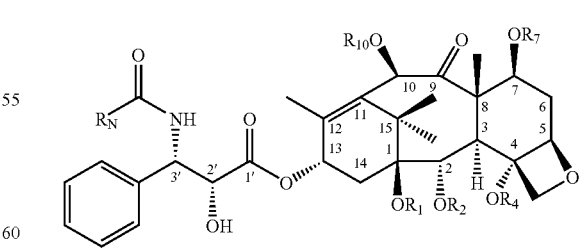

wherein
- $R_1$ is hydrogen;
- $R_2$ is a benzoyl group;
- $R_4$ is an acetate group;
- $R_7$ is hydrogen;

$R_{10}$ is hydrogen or an acetate group;

R is an alkoxy group, an alkyl group, an aryl group, an arylalkyl group, an ether group, heterocyclic group, or a vinyl group; and $R_N$ is phenyl, 1-methyl-1-propenyl, n-pentyl, propyl, 1-methyl-propyl, benzyl, 2-furanyl, or tert-butoxy;

the method comprising the steps of:
reacting the taxane molecule with zirconocene chloride hydride in a solvent to form an imine compound;
hydrolyzing the imine compound to form a primary amine compound; and
treating the primary amine compound with a base to form another taxane molecule having the formula:

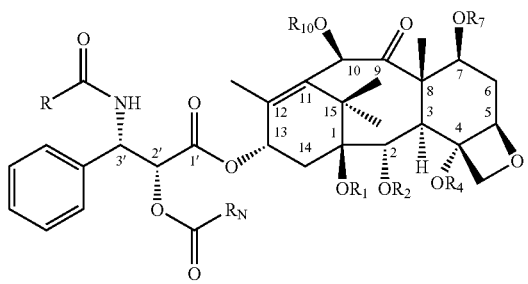

wherein
$R_1$, $R_2$, $R_4$, $R_7$, $R_{10}$, and $R_N$ are as defined above.

17. The method of claim 16 wherein the step of reacting the taxane molecule comprises reacting the taxane molecule with about 3 or more molar equivalents of zirconocene chloride hydride.

18. The method of claim 17 wherein reacting the taxane molecule with zirconocene chloride hydride comprises reacting the taxane molecule with zirconocene chloride hydride at a temperature below about 15° C.

19. The method of claim 16 wherein the solvent is tetrahydrofuran.

20. The method of claim 16 wherein the step of hydrolyzing the imine compound comprises treating the imine compound with an acid.

21. The method of claim 20, wherein the step of hydrolyzing the imine compound comprises treating the imine compound with sulfuric acid.

22. The method of claim 16, wherein the step of treating the primary amine compound with a base comprises treating the primary amine compound with triethylamine.

23. The method of claim 16, wherein the step of treating the primary amine compound with base comprises treating the primary amine compound with triethylamine and anthranilic acid.

24. The method of claim 16 comprising the step of chelating the zirconocene chloride hydride and other zirconium by-products prior to hydrolyzing the imine compound with a chelating agent.

25. The method of claim 16, wherein the chelating step comprises chelating the transition metal reducing agent or by-products thereof with N,N-bis(2-hydroxyethyl) glycine (bicine).

26. The method of claim 16, wherein the chelating step comprises chelating the transition metal reducing agent or by-products thereof with an agent comprising a chelating agent selected from the group consisting of ethylene diamine tetra acetic acid (EDTA), ethylene glycol (bis) aminoethyl ether tetra acetic acid (EGTA), 1,2-bis-(o-aminophenoxy) ethane-N,N,N',N'-tetraacetic acid (BAPTA), N,N,N',N'-tetrakis-(2-pyridylmethyl) ethylenediamine (TPEN), nitrilotriacetic acid, TIRON® and analogues and derivatives thereof.

27. The method of claim 16 wherein $R_{10}$ is hydrogen.

28. The method of claim 27 wherein $R_N$ is phenyl, and R is phenyl, 1-methyl-1-propenyl, n-pentyl, propyl, 1-methyl-propyl, benzyl, 2-furanyl, or tert-butoxy.

29. The method of claim 27 wherein $R_N$ is 1-methyl-1-propenyl, and R is phenyl, 1-methyl-1-propenyl, n-phetyl, propyl, 1-methyl-propyl, benzyl, 2-furanyl, or tert butoxy.

30. The method of claim 27 wherein $R_N$ is n-pentyl, and R is phenyl, 1-methyl-1-propenyl, n-pentyl, propyl, 1-methyl-propyl, benzyl, 2-furanyl, or tert-butoxy.

31. The method of claim 16 wherein $R_{10}$ is an acetate group.

32. The method of claim 31 wherein $R_N$ is phenyl, and R is phenyl, 1-methyl-1-propenyl, n-pentyl, propyl, 1-methyl-propyl, benzyl, 2-furanyl, or tert-butoxy.

33. The method of claim 31 wherein $R_N$ is 1-methyl-1-propenyl, and R is phenyl, 1-methyl-1-propenyl, n-phetyl, propyl, 1-methyl-propyl, benzyl, 2-furanyl, or tert butoxy.

34. The method of claim 31 wherein $R_N$ is n-pentyl, and R is phenyl, 1-methyl-1-propenyl, n-pentyl, propyl, 1-methyl-propyl, benzyl, 2-furanyl, or tert-butoxy.

35. The method of claim 34, further comprises the step of dictating the zirconocene chloride hydride and other zirconium by-products thereof by adding a chelating agent.

36. The method of claim 35, wherein the chelating step comprises adding zirconium chelator.

37. The method of claim 35, wherein the chelating step comprises chelating the transition metal reducing agent or by-products thereof with N,N-bis(2-hydroxyethyl)glycine (bicine).

38. The method of claim 35, wherein the chelating step comprises adding a chelating agent comprising a chelating agent selected from the group consisting of ethylene diamine tetra acetic acid (EDTA), ethylene glycol (bis) aminoethyl ether tetra acetic acid (EGTA), 1,2-bis-(O-aminophenoxy) ethane-N,N,N',N'-tetra-acetic acid (BAPTA), N,N,N',N'-tetrakis-(2-pyridylmethyl)ethylenediamine (TPEN), nitrilotriacetic acid, TIRON® or analogues thereof.

39. The method of claims 1 or 16, further comprising the step of removing substantially all of the transition metal or transition metal by-products by complexation, precipitation, filtration, centrifugation, electrochemical methodology, chromatography, chelation or any combination thereof.

40. A method of converting an acyl-protected taxane molecule, the method comprising the steps of:
reductively deoxygenating an amide group on the taxane molecule to form an imine compound;
hydrolyzing the imine compound to form a primary amine compound; and
treating the primary amine compound with a hindered base capable of effecting acyl migration to form another taxane molecule.

41. The method of claim 40, wherein the step of reductively deoxygenating an amide group on the taxane compound comprises conducting the taxane compound with a transition metal reducing agent.

42. The method of claim 40, wherein the step of hydrolyzing the imine compound comprises contacting the imine compound with an acid.

43. The method of claim 40, wherein the step of treating the primary amine compound with a base comprises treating the primary amine compound with triethylamine.

* * * * *

UNITED STATES PATENT AND TRADEMARK OFFICE
CERTIFICATE OF CORRECTION

PATENT NO. : 7,220,872 B2  
APPLICATION NO. : 10/510120  
DATED : May 22, 2007  
INVENTOR(S) : Johnson et al.

Page 1 of 1

It is certified that error appears in the above-identified patent and that said Letters Patent is hereby corrected as shown below:

Col. 20,  
Line 51: Delete "Lines 51-62" and insert

--
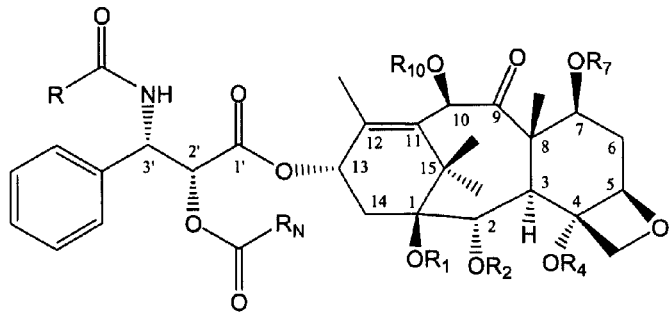
--

Col. 21,  
Line 14: Delete "Lines 14-27" and insert

--
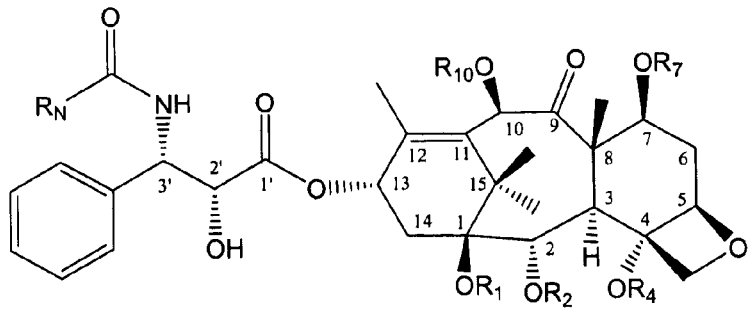
--

Signed and Sealed this

Twenty-fifth Day of March, 2008

JON W. DUDAS  
*Director of the United States Patent and Trademark Office*